(12) United States Patent
Gonzalez Suarez et al.

(10) Patent No.: US 12,097,494 B2
(45) Date of Patent: Sep. 24, 2024

(54) METHODS, DEVICES, AND SYSTEMS FOR DETECTING TWO OR MORE ANALYTES WITHIN SMALL VOLUMES

(71) Applicant: Mayo Foundation for Medical Education and Research, Rochester, MN (US)

(72) Inventors: Alan M. Gonzalez Suarez, Rochester, MN (US); Alexander Revzin, Rochester, MN (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 234 days.

(21) Appl. No.: 17/478,154

(22) Filed: Sep. 17, 2021

(65) Prior Publication Data
US 2022/0080417 A1    Mar. 17, 2022

Related U.S. Application Data

(60) Provisional application No. 63/079,917, filed on Sep. 17, 2020.

(51) Int. Cl.
| | | |
|---|---|---|
| *B01L 3/00* | (2006.01) | |
| *G01N 33/49* | (2006.01) | |
| *G01N 33/66* | (2006.01) | |

(52) U.S. Cl.
CPC ... *B01L 3/502715* (2013.01); *B01L 3/502753* (2013.01); *G01N 33/491* (2013.01);
(Continued)

(58) Field of Classification Search
CPC .......... B01L 2400/06; B01L 2400/046; B01L 2400/0655
See application file for complete search history.

(56) References Cited

U.S. PATENT DOCUMENTS 6,387,234 B1 * 5/2002 Yeung .............. G01N 27/44782
204/601
2007/0264629 A1 * 11/2007 Holmes ................. B01L 3/5027
435/5
(Continued)

FOREIGN PATENT DOCUMENTS

| CA | 2614311 | 1/2007 |
|---|---|---|
| WO | WO 2004061413 | 7/2004 |

OTHER PUBLICATIONS

Cedillo-Alcantar et al., "Automated Droplet-Based Microfluidic Platform for Multiplexed Analysis of Biochemical Markers in Small Volumes," Anal. Chemistry, Mar. 5, 2019, 91(8):5133-5141.
(Continued)

*Primary Examiner* — Maris R Kessel
*Assistant Examiner* — Alea N. Martin
(74) *Attorney, Agent, or Firm* — Fish & Richardson P.C.

(57) ABSTRACT

This document provides methods, devices, and systems for detecting the presence, absence, or amount of two or more analytes present within a small volume (e.g., less than 10 µL) of a sample (e.g., a blood sample) obtained from a mammal (e.g., a human such as a human neonate). For example, methods and materials for using plasma separation and multiplex analyte detection to detect two or more analytes (e.g., proteins, carbohydrates, lipids, nucleic acids, intact cells, intact viruses, intact microorganisms, and/or chemicals) within a small volume of a blood sample are provided.

8 Claims, 6 Drawing Sheets

(52) U.S. Cl.
CPC .......... *G01N 33/492* (2013.01); *G01N 33/66* (2013.01); *B01L 2200/16* (2013.01); *B01L 2300/0663* (2013.01); *B01L 2300/0681* (2013.01); *B01L 2300/0838* (2013.01); *B01L 2300/0867* (2013.01); *B01L 2300/0883* (2013.01); *B01L 2400/06* (2013.01)

(56) References Cited

U.S. PATENT DOCUMENTS

| | | | | |
|---|---|---|---|---|
| 2008/0003145 | A1* | 1/2008 | Nurse | B01L 3/502738 422/400 |
| 2012/0220047 | A1* | 8/2012 | Seifried | G01N 33/491 422/534 |
| 2016/0332163 | A1* | 11/2016 | Wang | B01J 19/0046 |
| 2017/0241977 | A1* | 8/2017 | Wilson | G01N 33/491 |

OTHER PUBLICATIONS

De Hoyos-Vega et al., "A versatile microfluidic device for multiple ex vivo/in vitro tissue assays unrestrained from tissue topography," Microsyst. Nanoengineering, Jun. 29, 2020, 6:40, 14 pages.

Dimov et al., "Stand-alone self-powered integrated microfluidic blood analysis system (SIMBAS)," Lab Chip, Dec. 8, 2010, 11(5):845-850.

Gonzalez-Suarez et al., "Dynamic Generation of Concentration- and Temporal-Dependent Chemical Signals in an Integrated Microfluidic Device for Single-Cell Analysis," Anal. Chemistry, Jun. 19, 2018, 90(14):8331-8336.

Grohmann et al., "Bilirubin Measurement for Neonates: Comparison of 9 Frequently Used Methods," Pediatrics, Apr. 2006, 117(4):1174-1183.

Lee et al., "3D-printed Quake-style microvalves and micropumps," Lab Chip, Mar. 9, 2018, 18(8):1207-1214.

Macallister et al., "Serial C-Reactive Protein Measurements in Newborn Infants without Evidence of Early-Onset Infection," Neonatology, May 21, 2019, 116(1):85-91.

SBIR.gov [online], "A microfluidic device for blood analysis in neonates," Sep. 19, 2019, retrieved on Dec. 30, 2021, retrieved from URL<https://www.sbir.gov/sbirsearch/detail/1683247>, 3 pages.

Spigarelli et al., "A passive two-way microfluidic device for low volume blood-plasma separation," Microelectron. Engineering, Mar. 15, 2019, 209:28-34.

Thorsen et al., "Microfluidic large-scale integration," Science, Oct. 18, 2002, 298(5593):580-584.

Unger et al., "Monolithic microfabricated valves and pumps by multilayer soft lithography," Science, Apr. 7, 2000, 288(5463):113-116.

Yeh et al., "Self-powered integrated microfluidic point-of-care low-cost enabling (SIMPLE) chip," Sci. Advances, Mar. 22, 2017, 3(3):e1501645, 12 pages.

* cited by examiner

METHODS, DEVICES, AND SYSTEMS FOR DETECTING TWO OR MORE ANALYTES WITHIN SMALL VOLUMES

CROSS-REFERENCE TO RELATED APPLICATIONS

This application claims the benefit of U.S. Patent Application Ser. No. 63/079,917, filed on Sep. 17, 2020. The disclosure of the prior application is considered part of (and is incorporated by reference in) the disclosure of this application.

BACKGROUND

1. Technical Field

This document provides methods, devices, and systems for detecting the presence, absence, or amount of two or more analytes present within a small volume (e.g., less than 10 µL) of a sample (e.g., a blood sample) obtained from a mammal (e.g., a human such as a human neonate). For example, this document provides methods and materials for using plasma separation and multiplex analyte detection to detect two or more analytes (e.g., proteins, carbohydrates, lipids, nucleic acids, intact cells, intact viruses, intact microorganisms, and/or chemicals) within a small volume of a blood sample.

2. Background Information

Premature newborns are vulnerable to hyperglycemia, infections, and jaundice. To test for these conditions, about 500 µL of blood is drawn for each biomarker, leading the infant to lose up to 20% of blood due to testing. There is a need for a blood analysis platform that can perform multi-analyte analysis in low blood volumes. Most microfluidic devices dedicated to blood analysis aim for plasma separation (Spigarelli et al., *Microelectronic Engineering*, 209:28-34 (2019)), require complicated immobilization of antibodies (Dimov et al., *Lab Chip*, 11:845-850 (2011)), or require large quantities of blood (≥50 µL) for further analysis (Yeh et al., *Science Advances*, 3:e1501645 (2017)).

SUMMARY

This document provides methods, devices, and systems for detecting the presence, absence, or amount of two or more analytes present within a small volume (e.g., less than 10 µL) of a sample (e.g., a blood sample) obtained from a mammal (e.g., a human such as a human neonate). For example, this document provides methods and materials for using plasma separation and multiplex analyte detection to detect two or more analytes (e.g., proteins, carbohydrates, lipids, nucleic acids, intact cells, intact viruses, intact microorganisms, and/or chemicals) within a small volume of a blood sample. As described herein, a microfluidic device can be designed to (a) separate plasma from 1 µL to 10 µL (e.g., about 5 µL) of whole blood and (b) analyze that separated small volume of plasma for the presence, absence, or amount of two or more (e.g., two, three, four, five, six, seven, eight, nine, or ten) analytes.

In general, one aspect of this document features a multiplexed analyte detection system comprising (or consisting essentially of or consisting of) (a) a sample inlet area for receiving a sample, (b) a channel fluidly connected to the inlet area via an inlet port and comprising (i) two or more serial sample chambers, wherein each of the two or more serial sample chambers comprises in inflow valve and an outflow valve along the channel, wherein the inflow valves and the outflow valves of each of the two or more serial sample chambers are controlled via a first master valve actuator port, and (ii) a vacuum port configured to allow application of a negative pressure to the channel, (c) a filter located between the inlet area and the channel and configured to filter the sample to allow a component of the sample to enter the channel when the negative pressure is applied via the vacuum port, and (d) two or more reagent chambers, wherein each of the two or more reagent chambers comprises a reaction control valve and is fluidly connected to one of the two or more serial sample chambers when the reaction control valve is open, thereby forming a reaction chamber, and is not in fluid communication with the one of the two or more serial sample chambers when the reaction control valve is closed, wherein the reaction control valves of each of the two or more reagent chambers are controlled via a second master valve actuator port. The sample can be whole blood. The channel from the inlet port to the vacuum port can be from 50 mm to 150 mm in length. The channel from the inlet port to the vacuum port can be from 100 µm to 140 µm in length. The channel can comprise a maximum volume within the channel from the inlet port to the vacuum port of from 0.75 µL to 2 µL. The channel can define two serial sample chambers. The channel can define three serial sample chambers. The channel can define four serial sample chambers. The channel can define five serial sample chambers. The channel can define six serial sample chambers. The vacuum port can be located at the end of the channel. The system comprises a positive pressure channel can comprise (i) a positive pressure control valve, and (ii) a positive pressure port configured to allow application of a positive pressure to the positive pressure channel, wherein the positive pressure channel is fluidly connected to the channel when the positive pressure control valve is open and is not in fluid communication with the channel when the positive pressure control valve is closed. The positive pressure channel can fluidly connect to the channel at a location located between the inlet port and the serial sample chambers. The channel can comprise a serpentine path, and wherein the positive pressure channel can fluidly connect to the channel at a location located between the inlet port and the serpentine path. The channel can comprise a sample cutoff valve located between the inlet port and the positive pressure channel. The channel can comprise a sample cutoff valve located between the inlet port and the serial sample chambers. The channel can comprise a serpentine path. The filter can be a plasma separation membrane. The component of the sample can be plasma. The sample inlet area can be configured to hold a maximum volume of the sample that is from 1 µL to 100 µL. The sample inlet area can be configured to hold a maximum volume of the sample that is from 50 µL to 10 µL. Each of the sample chambers can have a maximum volume from 30 nL to 100 nL. Each reaction chamber formed from one of the sample chambers and one of the reagent chambers when the reaction control valve located between those two chambers is open can have a maximum volume from 60 nL to 200 nL. The system can comprise reagents for detecting a first analyte if present within a sample chamber, wherein the reagents are located within one of the reagent chambers. The first analyte can be selected from the group consisting of glucose, bilirubin, an enzyme, a protein, a chemical molecule, and a carbohydrate. The system can comprise reagents for detecting a second analyte if present within a sample chamber, wherein the reagents can be located within a second one of the reagent chambers. The second analyte can be different from the first analyte, and wherein the second analyte can be selected from the group consisting of glucose, bilirubin, an enzyme, a protein, a chemical molecule, and a carbohydrate. The system can comprise two or more reagent channels, wherein each of the two or more reagent channels can comprise a reagent inlet port, a reagent outlet port, a reagent inflow valve along the reagent channel, and a reagent outflow valve along the reagent channel, wherein one of the two or more reagent chambers is formed along the reagent channel when the reagent inflow valve and the reagent outflow valve are closed. The reagent inflow valves and the reagent outflow valves of each of the two or more reagent channels can be controlled via the first master valve actuator port. Each of the two or more reagent channels can comprise a positive control reagent chamber and a negative control reagent chamber in series with the one of the two or more reagent chambers along the reagent channel, wherein the positive control reagent chamber is defined by a first additional valve and either the reagent inflow valve or the reagent outflow valve, and wherein the negative control reagent chamber is defined by a second additional valve and the other of the reagent inflow valve or the reagent outflow valve. The reagent inflow valves, the reagent outflow valves, the first additional valves, and the second additional valves of each of the two or more reagent channels can be controlled via the first master valve actuator port. The system can comprise a positive control sample channel comprising a positive sample inlet port, a positive sample outlet port, a positive sample inflow valve along the positive sample channel, a positive sample outflow valve along the positive sample channel, and a positive sample chamber, wherein the positive sample chamber is formed along the positive sample channel when the positive sample inflow valve and the positive sample outflow valve are closed. The system can comprise a separate positive control sample channel for each of the two or more serial sample chambers. The positive sample inflow and positive sample outflow valves can be controlled via the first master valve actuator port. The system can comprise a negative control sample channel comprising a negative sample inlet port, a negative sample outlet port, a negative sample inflow valve along the negative sample channel, a negative sample outflow valve along the negative sample channel, and a negative sample chamber, wherein the negative sample chamber is formed along the negative sample channel when the negative sample inflow valve and the negative sample outflow valve are closed. The system can comprise a separate negative control sample channel for each of the two or more serial sample chambers. The negative sample inflow and negative sample outflow valves can be controlled via the first master valve actuator port. Each of the two or more positive control reagent chambers can comprise a positive control reaction control valve and is fluidly connected to one of the positive control sample chambers when the positive control reaction control valve is open, thereby forming a positive control reaction chamber, and is not in fluid communication with the one of the two or more positive control sample chambers when the positive control reaction control valve is closed. The positive control reaction control valves of each of the two or more positive control reagent chambers can be controlled via the second master valve actuator port. Each of the two or more negative control reagent chambers can comprise a negative control reaction control valve and is fluidly connected to one of the negative control sample chambers when the negative control reaction control valve is open, thereby forming a negative control reaction chamber, and is not in fluid communication with the one of the two or more negative control sample chambers when the negative control reaction control valve is closed. The negative control reaction control valves of each of the two or more negative control reagent chambers can be controlled via the second master valve actuator port.

In another aspect, this document features a method for detecting the presence, absence, or amount of two or more analytes in a sample. The method comprises (or consisting essentially of or consisting of) (a) obtaining a multiplexed analyte detection system, (b) inserting from about 1 µL to about 10 µL of a sample into the sample inlet area, (c) applying negative pressure to the channel via the vacuum port, wherein the component of the sample is drawn into the two or more sample chambers, (d) actuating the first master valve actuator port to close the inflow valves and the outflow valves, (e) actuating the second master valve actuator port to open the reaction valves of each of the two or more reagent chambers, thereby allowing each reaction chamber to form, wherein the reagents of each of the two or more reagent chambers and the component of the sample of each of the two or more sample chambers within each formed reaction chamber mix to form a reaction mixture, and (f) detecting the presence, absence, or amount of analyte within each reaction mixture. The obtained multiplexed analyte detection system can comprise (or consist essentially of or consist of) (a) a sample inlet area for receiving a sample, (b) a channel fluidly connected to the inlet area via an inlet port and comprising (i) two or more serial sample chambers, wherein each of the two or more serial sample chambers comprises in inflow valve and an outflow valve along the channel, wherein the inflow valves and the outflow valves of each of the two or more serial sample chambers are controlled via a first master valve actuator port, and (ii) a vacuum port configured to allow application of a negative pressure to the channel, (c) a filter located between the inlet area and the channel and configured to filter the sample to allow a component of the sample to enter the channel when the negative pressure is applied via the vacuum port, and (d) two or more reagent chambers, wherein each of the two or more reagent chambers comprises a reaction control valve and is fluidly connected to one of the two or more serial sample chambers when the reaction control valve is open, thereby forming a reaction chamber, and is not in fluid communication with the one of the two or more serial sample chambers when the reaction control valve is closed, wherein the reaction control valves of each of the two or more reagent chambers are controlled via a second master valve actuator port. The sample can be whole blood. The channel from the inlet port to the vacuum port can be from 50 mm to 150 mm in length. The channel from the inlet port to the vacuum port can be from 100 µm to 140 µm in length. The channel can comprise a maximum volume within the channel from the inlet port to the vacuum port of from 0.75 µL to 2 µL. The channel can define two serial sample chambers. The channel can define three serial sample chambers. The channel can define four serial sample chambers. The channel can define five serial sample chambers. The channel can define six serial sample chambers. The vacuum port can be located at the end of the channel. The system comprises a positive pressure channel can comprise (i) a positive pressure control valve, and (ii) a positive pressure port configured to allow application of a positive pressure to the positive pressure channel, wherein the positive pressure channel is fluidly connected to the channel when the positive pressure control valve is open and is not in fluid communication with the channel when the positive pressure control valve is closed. The positive pressure channel can fluidly connect to the channel at a location located between the inlet port and the serial sample chambers. The channel can comprise a serpentine path, and wherein the positive pressure channel can fluidly connect to the channel at a location located between the inlet port and the serpentine path. The channel can comprise a sample cutoff valve located between the inlet port and the positive pressure channel. The channel can comprise a sample cutoff valve located between the inlet port and the serial sample chambers. The channel can comprise a serpentine path. The filter can be a plasma separation membrane. The component of the sample can be plasma. The sample inlet area can be configured to hold a maximum volume of the sample that is from 1 µL to 100 µL. The sample inlet area can be configured to hold a maximum volume of the sample that is from 50 µL to 10 µL. Each of the sample chambers can have a maximum volume from 30 nL to 100 nL. Each reaction chamber formed from one of the sample chambers and one of the reagent chambers when the reaction control valve located between those two chambers is open can have a maximum volume from 60 nL to 200 nL. The system can comprise reagents for detecting a first analyte if present within a sample chamber, wherein the reagents are located within one of the reagent chambers. The first analyte can be selected from the group consisting of glucose, bilirubin, an enzyme, a protein, a chemical molecule, and a carbohydrate. The system can comprise reagents for detecting a second analyte if present within a sample chamber, wherein the reagents can be located within a second one of the reagent chambers. The second analyte can be different from the first analyte, and wherein the second analyte can be selected from the group consisting of glucose, bilirubin, an enzyme, a protein, a chemical molecule, and a carbohydrate. The system can comprise two or more reagent channels, wherein each of the two or more reagent channels can comprise a reagent inlet port, a reagent outlet port, a reagent inflow valve along the reagent channel, and a reagent outflow valve along the reagent channel, wherein one of the two or more reagent chambers is formed along the reagent channel when the reagent inflow valve and the reagent outflow valve are closed. The reagent inflow valves and the reagent outflow valves of each of the two or more reagent channels can be controlled via the first master valve actuator port. Each of the two or more reagent channels can comprise a positive control reagent chamber and a negative control reagent chamber in series with the one of the two or more reagent chambers along the reagent channel, wherein the positive control reagent chamber is defined by a first additional valve and either the reagent inflow valve or the reagent outflow valve, and wherein the negative control reagent chamber is defined by a second additional valve and the other of the reagent inflow valve or the reagent outflow valve. The reagent inflow valves, the reagent outflow valves, the first additional valves, and the second additional valves of each of the two or more reagent channels can be controlled via the first master valve actuator port. The system can comprise a positive control sample channel comprising a positive sample inlet port, a positive sample outlet port, a positive sample inflow valve along the positive sample channel, a positive sample outflow valve along the positive sample channel, and a positive sample chamber, wherein the positive sample chamber is formed along the positive sample channel when the positive sample inflow valve and the positive sample outflow valve are closed. The system can comprise a separate positive control sample channel for each of the two or more serial sample chambers. The positive sample inflow and positive sample outflow valves can be controlled via the first master valve actuator port. The system can comprise a negative control sample channel comprising a negative sample inlet port, a negative sample outlet port, a negative sample inflow valve along the negative sample channel, a negative sample outflow valve along the negative sample channel, and a negative sample chamber, wherein the negative sample chamber is formed along the negative sample channel when the negative sample inflow valve and the negative sample outflow valve are closed. The system can comprise a separate negative control sample channel for each of the two or more serial sample chambers. The negative sample inflow and negative sample outflow valves can be controlled via the first master valve actuator port. Each of the two or more positive control reagent chambers can comprise a positive control reaction control valve and is fluidly connected to one of the positive control sample chambers when the positive control reaction control valve is open, thereby forming a positive control reaction chamber, and is not in fluid communication with the one of the two or more positive control sample chambers when the positive control reaction control valve is closed. The positive control reaction control valves of each of the two or more positive control reagent chambers can be controlled via the second master valve actuator port. Each of the two or more negative control reagent chambers can comprise a negative control reaction control valve and is fluidly connected to one of the negative control sample chambers when the negative control reaction control valve is open, thereby forming a negative control reaction chamber, and is not in fluid communication with the one of the two or more negative control sample chambers when the negative control reaction control valve is closed. The negative control reaction control valves of each of the two or more negative control reagent chambers can be controlled via the second master valve actuator port. The method can comprise detecting the amount of an analyte using a colorimetric assay for at least one of the reaction mixtures. The method can comprise detecting the amount of an analyte using a fluorescent-based assay for at least one of the reaction mixtures.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description below. Other features, objects, and advantages of the invention will be apparent from the description and drawings, and from the claims.

Similar results were achieved with both approaches as assessed measuring diluted bilirubin (D Bili), total bilirubin (T Bili), hemoglobin, and proteins.

Figure 4:
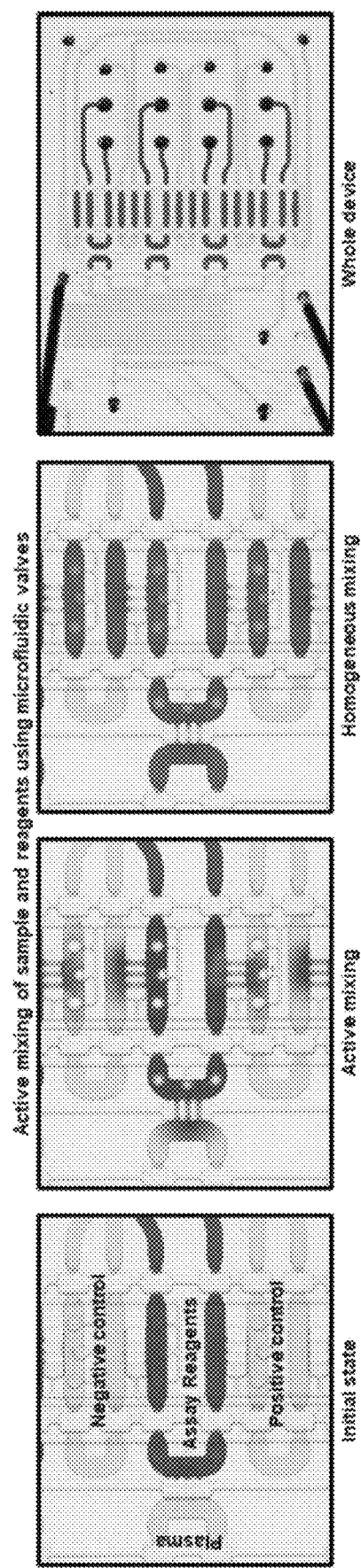

FIG. 4 contains four images showing the mixture of food dyes. A yellow food dye was used to represent samples, and a blue food dye was used to represent assay reagents. A green color demonstrates effective mixing.

Figure 5A:
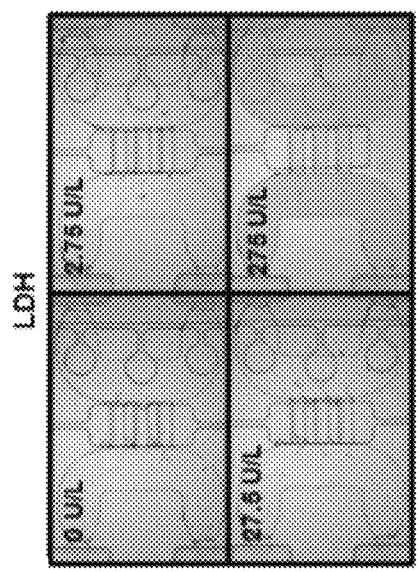
Figure 5A:
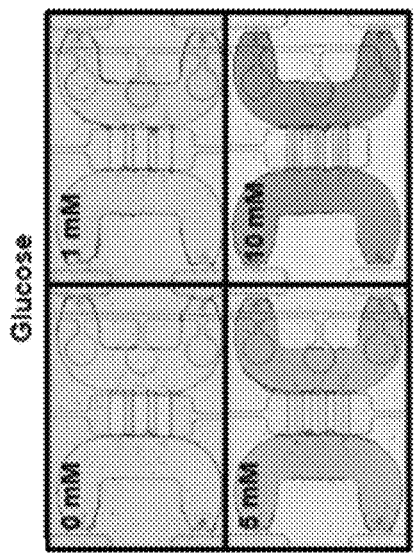
Figure 5B:
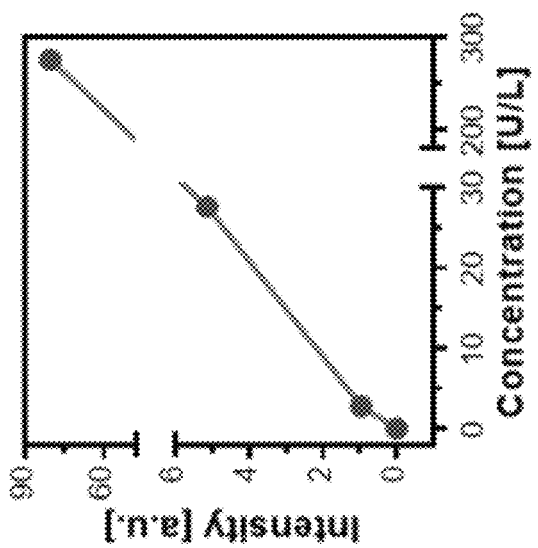
Figure 5B:
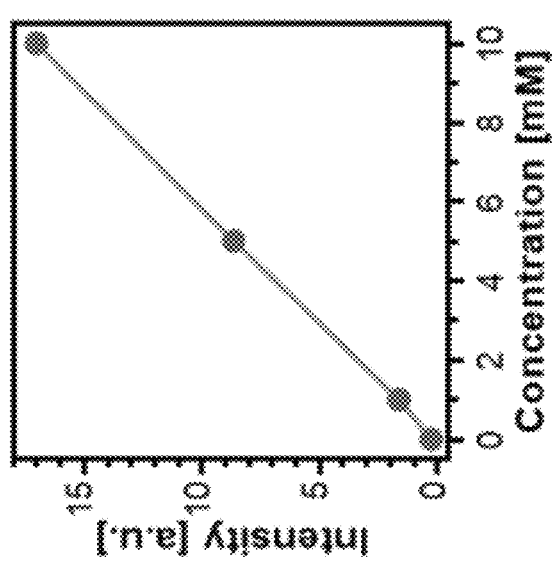

FIGS. 5A and 5B show results for reactions using the indicated amounts of D-glucose in a colorimetric assay (FIG. 5A) and the indicated amounts of LDH in a fluorescence-based assay.

Figure 6:
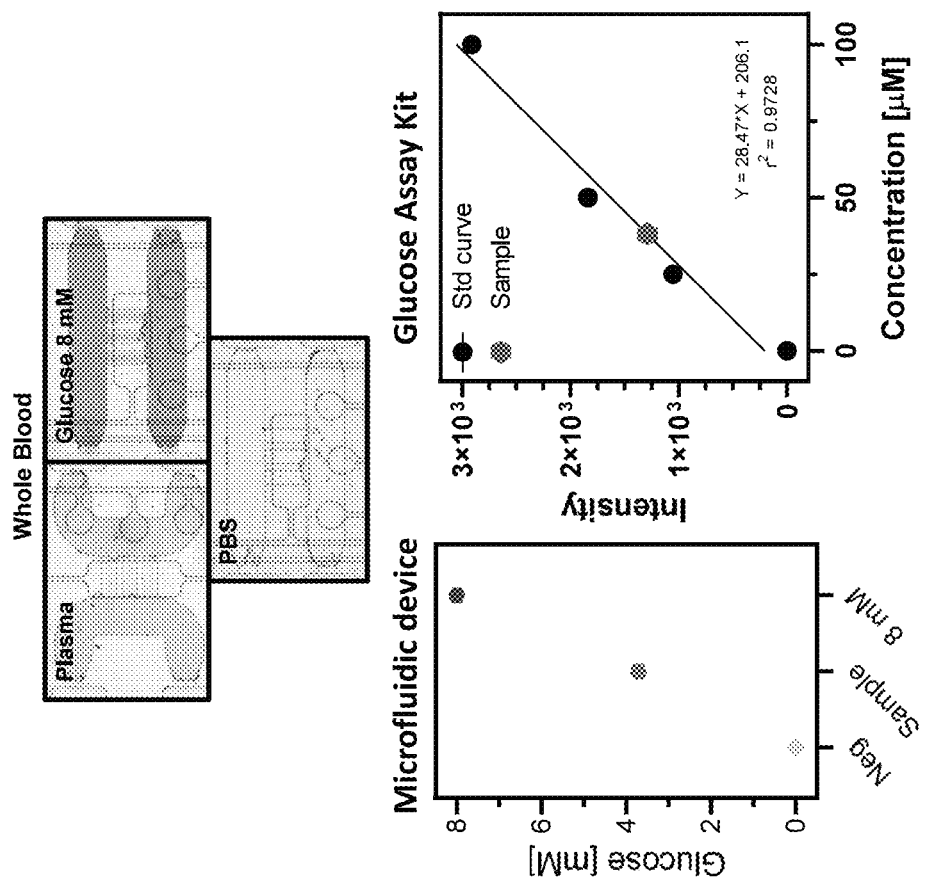

FIG. 6 shows results for measuring glucose in plasma separated from 5 μL of whole blood using a microfluidic device provided herein. PBS was used as a negative control, and a glucose solution (8 mM) was used as a positive control.

DETAILED DESCRIPTION

This document provides methods, devices, and systems for detecting the presence, absence, or amount of two or more analytes present within a small volume (e.g., less than 10 μL) of a sample (e.g., a blood sample) obtained from a mammal (e.g., a human such as a human neonate). For example, this document provides methods and materials for using plasma separation and multiplex analyte detection to detect two or more analytes (e.g., proteins, carbohydrates, lipids, nucleic acids, intact cells, intact viruses, intact microorganisms, and/or chemicals) within a small volume of a blood sample.

Any appropriate type of analytes can be detected using the methods and materials provided herein. For example, a device or system provided herein can be configured to detect the presence, absence, or amount of a protein, carbohydrate, lipid, nucleic acid, intact cell, intact virus, intact microorganism, and/or chemical. Examples of proteins that can be detected using the methods and materials provided herein include, without limitation, enzymes such as lactate dehydrogenase (LDH), alanine transaminase (ALT), aspartate transaminase (AST), creatine phosphokinase (CPK), and metalloproteases (e.g., ADAM12), receptors such as soluble chemokine receptors (e.g., CCRS and CXCR4), soluble growth factor receptors (e.g., EGFR), and soluble transferrin receptor, serum proteins such as albumin, transferrin, alpha-1 anti-trypsin, and immunoglobulins, inflammatory cytokines such as tumor necrosis factor alpha (TNF-α), interleukin 2 (IL-2), and interferon gamma (IFN-γ), viral proteins such as HIV envelope protein gp120 and E protein of SARS-CoV-2, bacterial proteins such as *Mycobacterium tuberculosis* surface protein Rv0227c and the MSCRAMM family of *S. aureus*, and fungal proteins such as Ssp1 and Sel1. Examples of carbohydrates that can be detected using the methods and materials provided herein include, without limitation, glucose, lactate, pyruvate, prostate-specific antigen (PSA), CA 125, and CA 19-9. Examples of lipids that can be detected using the methods and materials provided herein include, without limitation, total cholesterol, triglycerides, high density lipoprotein (HDL), and low density lipoprotein (LDL). Examples of intact viruses that can be detected using the methods and materials provided herein include, without limitation, human immunodeficiency viruses (e.g., HIV1 and HIV2), coronaviruses (e.g., COVID-19), Zika viruses, influenza viruses A and B, adenoviruses, RSV viruses, parainfluenza viruses, human metapneumoviruses, rhinoviruses, enteroviruses, hepatitis A, B, C and E viruses, rotaviruses, human papillomaviruses, measles viruses, caliciviruses, astroviruses, West Nile viruses, Ebola viruses, Dengue fever viruses, African swine fever viruses, herpes simplex viruses (e.g., HSV-2), Norwalk and Norwalk-like viruses, enteric adenoviruses, yellow fever viruses, chikungunya viruses, Epstein-Barr viruses, parvoviruses, varicella zoster viruses, and Ross River viruses. Examples of intact microorganisms that can be detected using the methods and materials provided herein include, without limitation, bacterial microorganisms such as *Staphylococcus aureus* (e.g., MRSA and MSSA), *Streptococcus pyogenes, Streptococcus pneumoniae, Mycoplasma pneumoniae, Haemophilus influenzae, Chlamydia pneumoniae, Bordelella pertussis, Mycobacterium tuberculosis, E. coli* (e.g., enterohaemorrhagic *E. coli* such as O157:H7 *E. coli* or enteropathogenic *E. coli*), *Salmonella* species (e.g., *Salmonella enterica*), *Listeria monocytogenes, Acinetobacter baumanni, Klebsiella oxytoca, Sarcoptes scabiei, Neisseria gonorrhoeae, Chlamydia trachomatis, Treponema pallidum, Campylobacter* species (e.g., thermophylic strains of *Campylobacter jejuni, C. lari,* or *C. coli*), *Bacillus cereus, Vibrio* species, *Yersinia enterocolitica, Shigella* species, *Enterococcus* species (e.g., *Enterococcus faecalis* or *E. faecium*), *Helicobacter pylori*, and *Clostridium* species (e.g., *Clostridium botulinum* or *Clostridium perfringens*), fungal microorganisms such as *Aspergillus* species (e.g., *A. flavus, A. fumigatus,* and *A. niger*), yeast (e.g., *Candida norvegensis* and *C. albicans*), *Penicillium* species, *Rhizopus* species, and *Alternaria* species, and protozoan microorganisms such as *Cryptosporidium parvum, Giardia lamblia,* and *Toxoplasma gondii*. Examples of chemicals that can be detected using the methods and materials provided herein include, without limitation, bilirubin, parathyroid hormone, bile acid, and urea.

Any appropriate sample can be assessed (e.g., for the presence, absence, or amount of one or more analytes) using the methods and materials (e.g., devices and systems) provided herein. In some cases, a sample can be a biological sample. For example, a sample can contain whole cells, cellular fragments, DNA, RNA, carbohydrates, lipids, viruses, microorganisms, and/or proteins. Examples of samples that can be used in the methods, devices, and systems described herein include, without limitation, whole blood samples, serum samples, plasma samples, urine samples, saliva samples, mucus samples, sputum samples, bronchial lavage samples, fecal samples, buccal samples, nasal samples, amniotic fluid samples, cerebrospinal fluid samples, synovial fluid samples, pleural fluid samples, pericardial fluid samples, peritoneal fluid samples, urethral samples, cervical samples, genital sore samples, hair samples, and skin samples.

In some cases, a sample to be assessed (e.g., for the presence, absence, or amount of one or more analytes) using the methods and materials (e.g., devices and systems) provided herein can be an environmental sample, a water sample, a soil sample, a food sample, a meat sample, a produce sample, a drink sample, a plant sample, a leaf sample, a root sample, a flower sample, a stem sample, a pollen sample, a seed sample, or an industrial sample (e.g., an air filter sample, sample collected from a work station, or a sample collected from a storage facility).

In some cases, the devices and systems provided herein can retain the sample within the device for safe and clean disposal.

A sample to be assessed (e.g., for the presence, absence, or amount of one or more analytes) using the methods and materials (e.g., devices and systems) provided herein can be obtained using any appropriate technique. For example, biological samples can be obtained using non-invasive (e.g., swab) techniques or invasive techniques (e.g., venipuncture, finger stick, or biopsy). In some cases, a whole blood sample can be obtained from a human (e.g., a human neonate) using a glass capillary tube. For example, an environmental sample and/or an industrial sample can be obtained using a surface swab technique. In some cases, a sample can be a liquid sample.

A liquid sample can be any appropriate volume. As described herein, very small volumes of a sample can be collected and accurately analyzed for the presence, absence, or amount of two or more analytes using the methods and materials provided herein. For example, a liquid sample (e.g., a whole blood sample) with a volume of about 1 µL to about 10 µL (e.g., from 1 µL to 10 µL, from 2 µL to 10 µL, from 3 µL to 10 µL, from 4 µL to 10 µL, from 1 µL to 9 µL, from 1 µL to 8 µL, from 1 µL to 7 µL, from 1 µL to 6 µL, from 2 µL to 8 µL, from 3 µL to 7 µL, or from 4 µL to 6 µL) can be obtained and analyzed for the presence, absence, or amount of two or more analytes using the methods and materials provided herein. In some cases, a larger volume can be obtained from the source, and a small portion (e.g., a volume from 1 µL to 10 µL, from 2 µL to 10 µL, from 3 µL to 10 µL, from 4 µL to 10 µL, from 1 µL to 9 µL, from 1 µL to 8 µL, from 1 µL to 7 µL, from 1 µL to 6 µL, from 2 µL to 8 µL, from 3 µL to 7 µL, or from 4 µL to 6 µL) of that larger obtained volume can be used in the methods and materials (e.g., device or system) described herein.

A sample to be assessed (e.g., for the presence, absence, or amount of one or more analytes) using the methods or materials (e.g., devices or systems) provided herein can be obtained from any appropriate animal. In some cases, a sample to be assessed as described herein can be obtained from a mammal (e.g., a human such as a human neonate, human baby, human toddler, human child, or human adult). Examples of mammals that samples can be obtained from include, without limitation, primates (e.g., humans and monkeys), dogs, cats, horses, cows, pigs, sheep, rabbits, and rodents (e.g., mice and rats). Other examples of animals that samples can be obtained from include, without limitation, fish, avian species (e.g., chickens, turkeys, ostrich, emus, cranes, and falcons) and non-mammalian animals (e.g., mollusks, frogs, lizards, snakes, and insects).

In some cases, a sample to be inserted into a device or system described herein can be obtained from a source (e.g., a human neonate) and directly inserted into the device or system without being pre-processed. For example, a whole blood sample can be obtained from a mammal (e.g., a human such as a human neonate) and directly inserted into a device or system provided herein without being pre-processed (e.g., without being treated or manipulated in any way).

In some cases, a sample to be inserted into a device or system described herein can be obtained from a source (e.g., a mammal or surface) and processed prior to being inserted into the device or system (e.g., can be pre-processed). Samples that are pre-processed can be pre-processed using one or more appropriate reagents (e.g., enzymes, acids, bases, buffers, detergents, anticoagulants, and/or aptamers) and/or techniques (e.g., purification techniques, centrifugation techniques, amplification techniques, culturing techniques, and/or denaturing techniques). For example, a blood sample can be obtained from a mammal (e.g., a human) and treated with one or more anticoagulants. Examples of anticoagulants that can be used to pre-process a sample (e.g., a blood sample) include, without limitation, EDTA, citrate (trisodium citrate), heparinates (e.g., sodium, lithium, or ammonium salt of heparin or calcium-titrated heparin), and hirudin. In some cases, a sample (e.g., a sample suspected to contain a microorganism) to be inserted into a device or system described herein can be obtained from a source (e.g., a food preparation surface) and pre-processed by culturing the sample with appropriate culture media for a period of time (e.g., 4 hours to 24 hours) prior to being inserted into the device or system. Examples of other pre-processing techniques that can be performed prior to inserting the sample into a device or system described herein include, without limitation, centrifugation to obtain cell-containing material, centrifugation to obtain cell-free material, filtration to remove cell containing material, cell lysis, nucleic acid purification, protein purification, nucleic acid amplification (e.g., polymerase chain reaction (PCR)), reverse transcription to obtain cDNA, reverse transcription PCR, nucleic acid denaturation, and isothermal amplification.

In some cases, the methods and materials provided herein can be used in small animal research, neonatal blood analysis, analysis of blood for one or more cardiac biomarkers, point-of-care testing of infectious diseases (e.g., COVID-19, sexually transmitted diseases, or HIV), and/or point-of-care testing in an operating room to provide rapid turnaround results.

Figure 1:
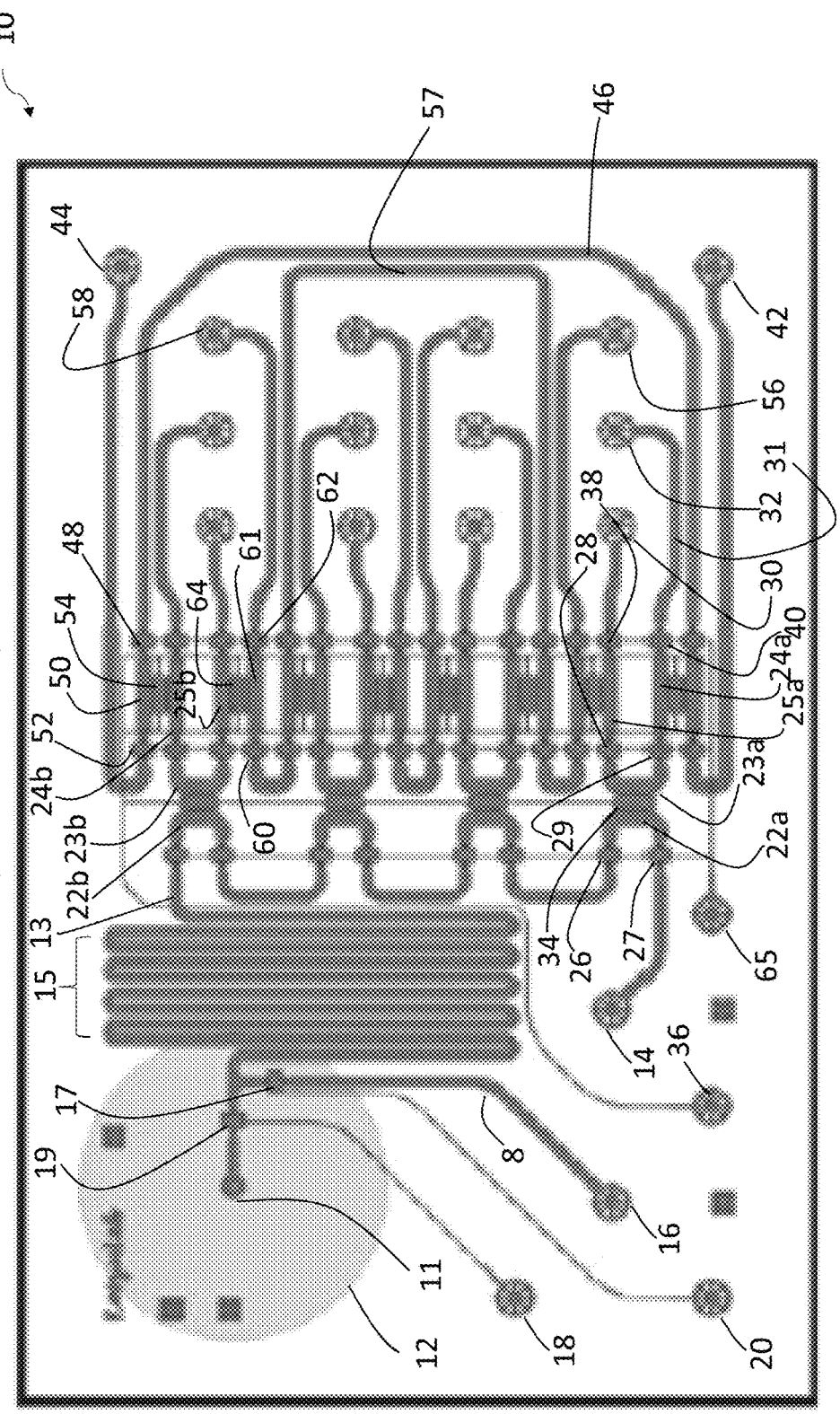
FIG. 1 is a schematic of a microfluidic device for plasma separation and analysis according to some embodiments.
Figure 2:
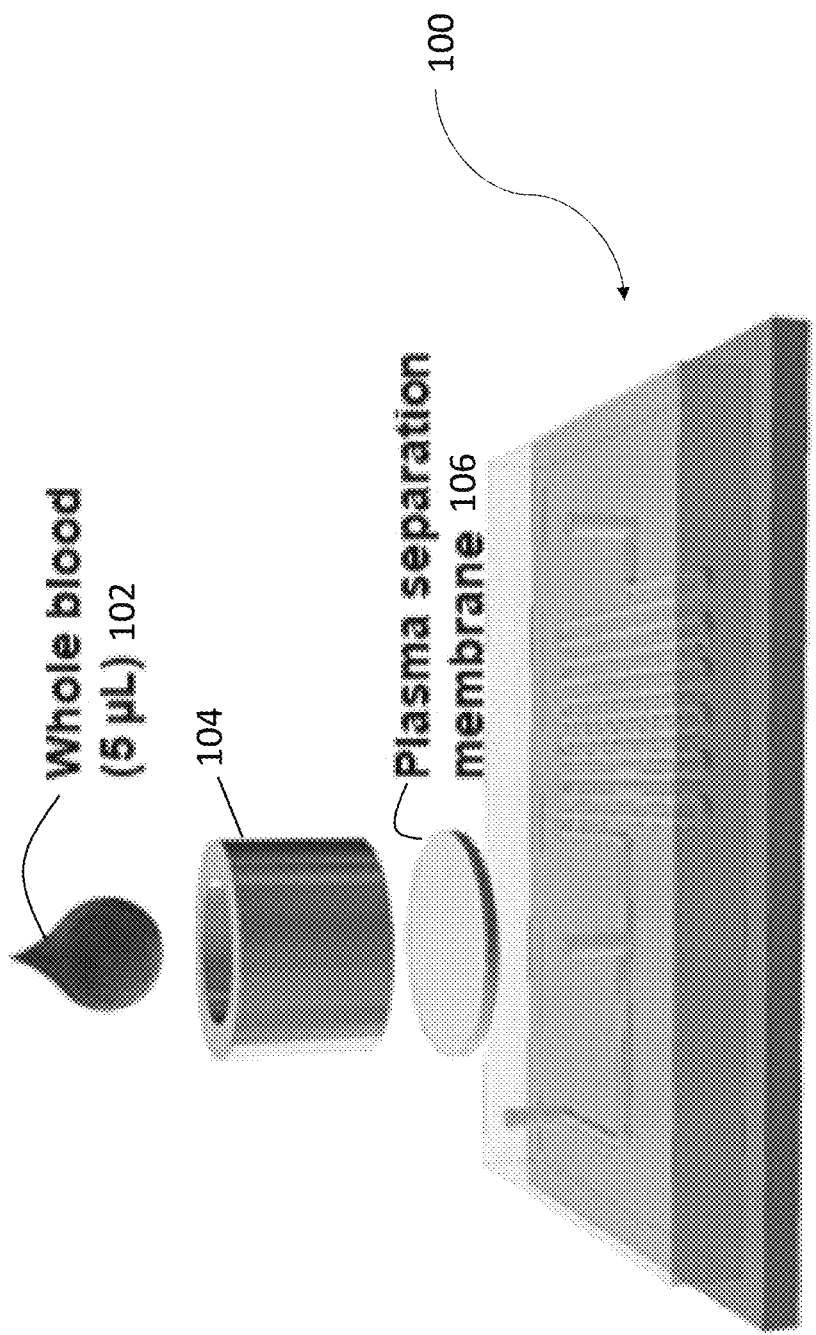
FIG. 2 is a schematic of a plasma separation system of a microfluidic device using a plasma separation membrane and 5 µL of blood according to some embodiments.

In some embodiments, with reference to FIGS. 1 and 2, microfluidic device 10 can include a sample inlet area 104. Sample inlet area 104 can be designed to receive and hold a volume of a sample ranging from 1 µL to 100 µL (e.g., from 1 µL to 75 µL, from 1 µL to 50 µL, from 1 µL to 25 µL, from 10 µL to 100 µL, from 25 µL to 100 µL, from 50 µL to 100 µL, from 25 µL to 75 µL, from 1 µL to 10 µL, from 2 µL to 10 µL, from 3 µL to 10 µL, from 4 µL to 10 µL, from 1 µL to 9 µL, from 1 µL to 8 µL, from 1 µL to 7 µL, from 1 µL to 6 µL, from 2 µL to 8 µL, from 3 µL to 7 µL, or from 4 µL to 6 µL).

Microfluidic device 10 can include an inlet 11 of channel 13 to receive the sample or a portion of the sample that was inserted into sample inlet area 104. In some cases, a filter or membrane 106 (e.g., a plasma separation membrane) can be located between sample inlet area 104 and inlet 11 to restrict at least some material of an inserted sample from entering channel 13. For example, when microfluidic device 10 includes plasma separation membrane 106 and whole blood is inserted into sample inlet area 104, plasma can be allowed to enter channel 13 while cells within the sample are restricted from entering channel 13.

In some cases, microfluidic device 10 can include a vacuum port configured to apply negative pressure to channel 13. In such cases, application of negative pressure can draw a sample or a portion of a sample from sample inlet area 104 into channel 13. In some cases, channel 13 can include a serpentine path 15. Channel 13 can have any appropriate length. In some cases, channel 13 can have a length from inlet 11 to vacuum port 14 that is from 10 mm to 200 mm (e.g., from 15 mm to 200 mm, from 25 mm to 200 mm, from 50 mm to 200 mm, from 75 mm to 200 mm, from 100 mm to 200 mm, from 10 mm to 175 mm, from 10 mm to 150 mm, from 25 mm to 150 mm, from 35 mm to 150 mm, from 50 mm to 150 mm, from 75 mm to 150 mm, from 100 mm to 150 mm, from 50 mm to 175 mm, from 75 mm to 175 mm, from 100 mm to 175 mm, from 125 mm to 175 mm, from 130 mm to 140 mm, from 125 mm to 145 mm, or 120 mm to 150 mm). Channel 13 can hold any appropriate volume of sample material. In some cases, channel 13 can hold a maximum volume from inlet 11 to vacuum port 14 that is from 0.5 µL to 5 µL (e.g., from 0.5 µL to 5 µL, from 0.75 µL to 5 µL, from 1 µL to 5 µL, from 1.5 µL to 5 µL, from 2 µL to 5 µL, from 0.5 µL to 4.5 µL, from 0.5 µL to 4 µL, from 0.5 µL to 3.5 µL, from 0.5 µL to 3 µL, from 0.5 µL to 2.5 µL, from 0.5 µL to 2 µL, from 0.75 µL to 2 µL, or from 1 µL to 2 µL).

In some cases, microfluidic device 10 can include a positive pressure port 16, a positive pressure channel 8, a positive pressure actuator port 20, a positive pressure valve 17, a sample cutoff actuator port 18, and a sample cutoff valve 19. Positive pressure valve 17 can be closed and sample cutoff valve 19 can be open while negative pressure is being applied to vacuum port 14 to draw sample from sample inlet area 12 into channel 13, for example, along serpentine path 15. Once an adequate volume of sample is drawn into channel 13 via negative pressure, sample cutoff actuator port 18 can be activated to close sample cutoff valve 19, and positive pressure actuator port 20 can be activated to open positive pressure valve 17. At this point, positive pressure can be applied to positive pressure port 16 to provide positive pressure to positive pressure channel 8 and channel 13 to move sample within channel 13 to the one or more sample chambers 22 of channel 13. FIG. 1 shows four sample chambers with the sample chamber of the lower part of FIG. 1 being labelled as sample chamber 22a and with the sample chamber of the upper part of FIG. 1 being labelled as sample chamber 22b. Microfluidic device 10 can include any appropriate number of sample chambers. For example, microfluidic device 10 can be configured to have one, two, three, four, five, six, seven, eight, nine, ten, or more sample chambers.

As shown in FIG. 1, the one or more sample chambers 22 of channel 13 can be in series along channel 13. In some cases, each of sample chamber 22 of channel 13 is defined by an inflow valve 26 and an outflow valve 27. Each sample chamber 22 of channel 13 defined by inflow valve 26 and outflow valve 27 can be designed to hold any appropriate volume of sample material. In some cases, each sample chamber 22 can hold a maximum volume that is from 20 nL to 500 nL (e.g., from 20 nL to 475 nL, from 20 nL to 450 nL, from 20 nL to 425 nL, from 20 nL to 400 nL, from 20 nL to 350 nL, from 20 nL to 300 nL, from 20 nL to 250 nL, from 20 nL to 200 nL, from 20 nL to 150 nL, from 20 nL to 100 nL, from 20 nL to 75 nL, from 20 nL to 50 nL, from 30 nL to 500 nL, from 35 nL to 500 nL, from 30 nL to 100 nL, from 30 nL to 75 nL, from 30 nL to 50 nL, or from 35 nL to 45 nL). While loading each sample chamber 22 with sample, inflow valves 26 and outflow valves 27 along channel 13 can be open. Once each sample chamber 22 is loaded with sample, a master valve actuator port 65 can be activated to close inflow valves 26 and outflow valves 27 along channel 13 and isolate sample within each sample chamber 22.

With further reference to FIG. 1, microfluidic device 10 can include one or more reagent chambers 23. FIG. 1 shows four reagent chambers with the reagent chamber of the lower part of FIG. 1 being labelled as reagent chamber 23a and with the reagent chamber of the upper part of FIG. 1 being labelled as reagent chamber 23b. Microfluidic device 10 can include any appropriate number of reagent chambers. For example, microfluidic device 10 can be configured to have one, two, three, four, five, six, seven, eight, nine, ten, or more reagent chambers. Typically, one sample chamber 22 is configured to be in fluid communication with one reagent chamber 23 when a reaction control valve 34 located between them is open. For example, sample chamber 22a is in fluid communication with reagent chamber 23a when reaction control valve 34 is open. When reaction control valve 34 is closed, sample chamber 22a and reagent chamber 23a are not in fluid communication.

As shown in FIG. 1, microfluidic device 10 can include a master valve actuator port 36 configured to control each reaction control valve 34. In some cases, however, microfluidic device 10 can include a separate valve actuator port to control each reaction control valve 34 independently.

In some cases, each of reagent chambers 23 is defined by a reagent inflow valve 28 and a reagent outflow valve 29. Each reagent chamber 23 defined by reagent inflow valve 28 and reagent outflow valve 29 can be designed to hold any appropriate volume of reagent(s). In some cases, each reagent chamber 23 can hold a maximum volume that is from 20 nL to 500 nL (e.g., from 20 nL to 475 nL, from 20 nL to 450 nL, from 20 nL to 425 nL, from 20 nL to 400 nL, from 20 nL to 350 nL, from 20 nL to 300 nL, from 20 nL to 250 nL, from 20 nL to 200 nL, from 20 nL to 150 nL, from 20 nL to 100 nL, from 20 nL to 75 nL, from 20 nL to 50 nL, from 30 nL to 500 nL, from 35 nL to 500 nL, from 30 nL to 100 nL, from 30 nL to 75 nL, from 30 nL to 50 nL, or from 35 nL to 45 nL). While loading each reagent chamber 23 with reagent(s), reagent inflow valves 28 and reagent outflow valves 29 along reagent channel 31 can be open. Once each reagent chamber 23 is loaded with reagent(s), a master valve actuator port 65 can be activated to close reagent inflow valves 28 and reagent outflow valves 29 along channel 31 and isolate reagent(s) within each reagent chamber 23.

Microfluidic device 10 can include a reagent inlet port 30 and reagent outlet port 32 for loading reagent(s) into reagent channel 31. Any appropriate reagent or set of reagents can be loaded into a reagent chamber 23. For example, when microfluidic device 10 is designed to detect glucose in a plasma sample, glucose oxidase, horseradish peroxidase, 4-aminoantipyrine (4-AAP), and ADOS reagents can be loaded into reagent chamber 23a and reagent chamber 23a can be designated for glucose detection. When that same microfluidic device 10 is designed to also detect direct bilirubin in a plasma sample, hydrochloric acid, sulfanilic acid, sodium nitrite, and sodium bicarbonate reagents can be loaded into reagent chamber 23b and reagent chamber 23b can be designated for bilirubin detection.

In some cases, microfluidic device 10 can include the ability to perform similar assays being performed on the sample (e.g., a plasma sample) inserted into sample inlet area 12 on a positive control sample, a negative control sample, or both a positive control sample and a negative control sample. For example, microfluidic device 10 can include an additional valve 38 along reagent channel 31 to create a negative control reagent chamber 25 and/or an additional valve 40 along reagent channel 31 to create a positive control reagent chamber 24. FIG. 1 shows four negative control reagent chambers with the negative control reagent chamber of the lower part of FIG. 1 being labelled as negative control reagent chamber 25a and with the negative control reagent chamber of the upper part of FIG. 1 being labelled as negative control reagent chamber 25b. FIG. 1 also shows four positive control reagent chambers with the positive control reagent chamber of the lower part of FIG. 1 being labelled as positive control reagent chamber 24a and with the positive control reagent chamber of the upper part of FIG. 1 being labelled as positive control reagent chamber 24b.

Each positive control reagent chamber 24 and/or each negative control reagent chamber 25 can be loaded with reagent(s) as each reagent chamber 23 are being loaded. For example, positive control reagent chamber 24a, negative control reagent chamber 25*a*, and reagent chamber 23*a* can be loaded with the same reagent(s) via reagent inlet port 30. As another example, positive control reagent chamber 24*b*, negative control reagent chamber 25*b*, and reagent chamber 23*b* can be loaded with the same reagent(s) via their corresponding reagent inlet port.

Once each positive reagent chamber 24 and/or negative reagent chamber 25 is loaded with reagent(s), master valve actuator port 65 can be activated to close reagent inflow valves 28, reagent outflow valves 29, additional valves 38, and additional valves 40 along reagent channel 31 and to isolate reagent(s) within reagent chamber 23, positive reagent chamber 24, and/or negative reagent chamber 25.

In some cases, positive reagent chamber 24 and/or negative reagent chamber 25 for each reagent chamber 23 can be configured to hold the same volume as that reagent chamber 23.

When microfluidic device 10 includes a positive control for a particular assay, microfluidic device 10 can include a positive sample inlet port 42, a positive sample outlet port 44, a positive control sample channel 46, a positive sample inflow valve 48 along positive control sample channel 46, a positive sample outflow valve 52 along positive control sample channel 46, and a positive sample chamber 50 defined by positive sample inflow valve 48 and positive sample outflow valve 52.

Each positive sample chamber 50 defined by positive sample inflow valve 48 and positive sample outflow valve 52 can be designed to hold any appropriate volume of positive control material. In some cases, each positive sample chamber 50 can hold a maximum volume that is from 20 nL to 500 nL (e.g., from 20 nL to 475 nL, from 20 nL to 450 nL, from 20 nL to 425 nL, from 20 nL to 400 nL, from 20 nL to 350 nL, from 20 nL to 300 nL, from 20 nL to 250 nL, from 20 nL to 200 nL, from 20 nL to 150 nL, from 20 nL to 100 nL, from 20 nL to 75 nL, from 20 nL to 50 nL, from 30 nL to 500 nL, from 35 nL to 500 nL, from 30 nL to 100 nL, from 30 nL to 75 nL, from 30 nL to 50 nL, or from 35 nL to 45 nL). While loading each positive sample chamber 50 with positive control material, positive sample inflow valve 48 and positive sample outflow valve 52 along positive control sample channel 46 can be open and positive control material can be inserted into positive sample inlet port 42. Once each positive sample chamber 50 is loaded with positive control material, a master valve actuator port 65 can be activated to close positive sample inflow valve 48 and positive sample outflow valve 52 along positive control sample channel 46 and isolate positive control material within each positive sample chamber 50.

In some cases, one positive sample chamber 50 is configured to be in fluid communication with one positive control reagent chamber 24 when a positive control reaction control valve 54 located between them is open. For example, positive sample chamber 50 is in fluid communication with positive control reagent chamber 24*b* when positive control reaction control valve 54 is open. When positive control reaction control valve 54 is closed, positive sample chamber 50 and positive control reagent chamber 24*b* are not in fluid communication.

As shown in FIG. 1, microfluidic device 10 can include a master valve actuator port 36 configured to control each positive control reaction control valve 54. In some cases, however, microfluidic device 10 can include a separate valve actuator port to control each positive control reaction control valve 54 independently.

When microfluidic device 10 includes a negative control for a particular assay, microfluidic device 10 can include a negative sample inlet port 56, a negative sample outlet port 58, a negative control sample channel 57, a negative sample inflow valve 60 along negative control sample channel 57, a negative sample outflow valve 62 along negative control sample channel 57, and a negative sample chamber 61 defined by negative sample inflow valve 60 and negative sample outflow valve 62.

Each negative sample chamber 61 defined by negative sample inflow valve 60 and negative sample outflow valve 62 can be designed to hold any appropriate volume of negative control material. In some cases, each negative sample chamber 61 can hold a maximum volume that is from 20 nL to 500 nL (e.g., from 20 nL to 475 nL, from 20 nL to 450 nL, from 20 nL to 425 nL, from 20 nL to 400 nL, from 20 nL to 350 nL, from 20 nL to 300 nL, from 20 nL to 250 nL, from 20 nL to 200 nL, from 20 nL to 150 nL, from 20 nL to 100 nL, from 20 nL to 75 nL, from 20 nL to 50 nL, from 30 nL to 500 nL, from 35 nL to 500 nL, from 30 nL to 100 nL, from 30 nL to 75 nL, from 30 nL to 50 nL, or from 35 nL to 45 nL). While loading each negative sample chamber 61 with negative control material, negative sample inflow valve 60 and negative sample outflow valve 62 along negative control sample channel 57 can be open and negative control material can be inserted into negative sample inlet port 56. Once each negative sample chamber 61 is loaded with negative control material, a master valve actuator port 65 can be activated to close negative sample inflow valve 60 and negative sample outflow valve 62 along negative control sample channel 57 and isolate negative control material within each negative sample chamber 61.

In some cases, one negative sample chamber 61 is configured to be in fluid communication with one negative control reagent chamber 25 when a negative control reaction control valve 64 located between them is open. For example, negative sample chamber 61 is in fluid communication with negative control reagent chamber 25*b* when negative control reaction control valve 64 is open. When negative control reaction control valve 64 is closed, negative sample chamber 61 and negative control reagent chamber 25*b* are not in fluid communication.

As shown in FIG. 1, microfluidic device 10 can include a master valve actuator port 36 configured to control each negative control reaction control valve 64. In some cases, however, microfluidic device 10 can include a separate valve actuator port to control each negative control reaction control valve 64 independently.

In some cases, microfluidic device 10 can include a master valve actuator port 36 configured to control each reaction control valve 34, each positive control reaction control valve 54, and each negative control reaction control valve 64.

Any appropriate method can be used to make a microfluidic device provided herein. For example, multilayer soft lithography techniques such as those described elsewhere (Unger et al., *Science*, 288:113-116 (2000); Gonzalez-Suarez et al., *Anal. Chem.*, 90:8331-8336 (2018); and de Hoyos-Vega et al., *Microsystems Nanoeng.*, 6:40 (2020)) can be used to make a microfluidic device provided herein. Any appropriate type of microfluidic valve and actuator port can be used as a valve and actuator port described herein. For example, valves and actuator ports such as those described elsewhere (Thorsen et al., *Science*, 298:580-584 (2002); and Lee et al., *Lab Chip*, 18:1207-1214 (2018)) can be used to make one or more of the valves and actuator ports described herein.

The invention will be further described in the following examples, which do not limit the scope of the invention described in the claims.

EXAMPLES

Example 1—Microfluidic Device for Plasma Separation and Analysis of Biomarkers Using 5 μL of Whole Blood A microfluidic device 10 comprising two layers was fabricated by multilayer soft lithography (FIG. 1). It included a module to separate plasma from 5 μL of whole blood by using a plasma separation membrane system (PSM, Cobetter Filtration; see items 104 and 106 of FIG. 2) and an assay module for up to four different biomarkers (FIG. 1). Plasma was separated by applying negative pressure to vacuum port 14 to pull plasma into a long microchannel 13 that can hold a volume of 1 μL. A plasma separation to membrane 106 (PSM; Cobetter Filtration) prevents blood cells from moving into the microchannel. Plasma was pushed to four sample chambers 22 using positive pressure applied at positive pressure port 16 and then isolated for testing using inflow valves 26 and outflow valves 27 for each sample chamber. The inflow and outflow values were controlled using master valve activator port 65. Assay reagents were previously loaded into device 10 and then actively mixed with plasma to develop the desired reaction. Positive and negative controls were tested simultaneously with plasma.

Figure 3:
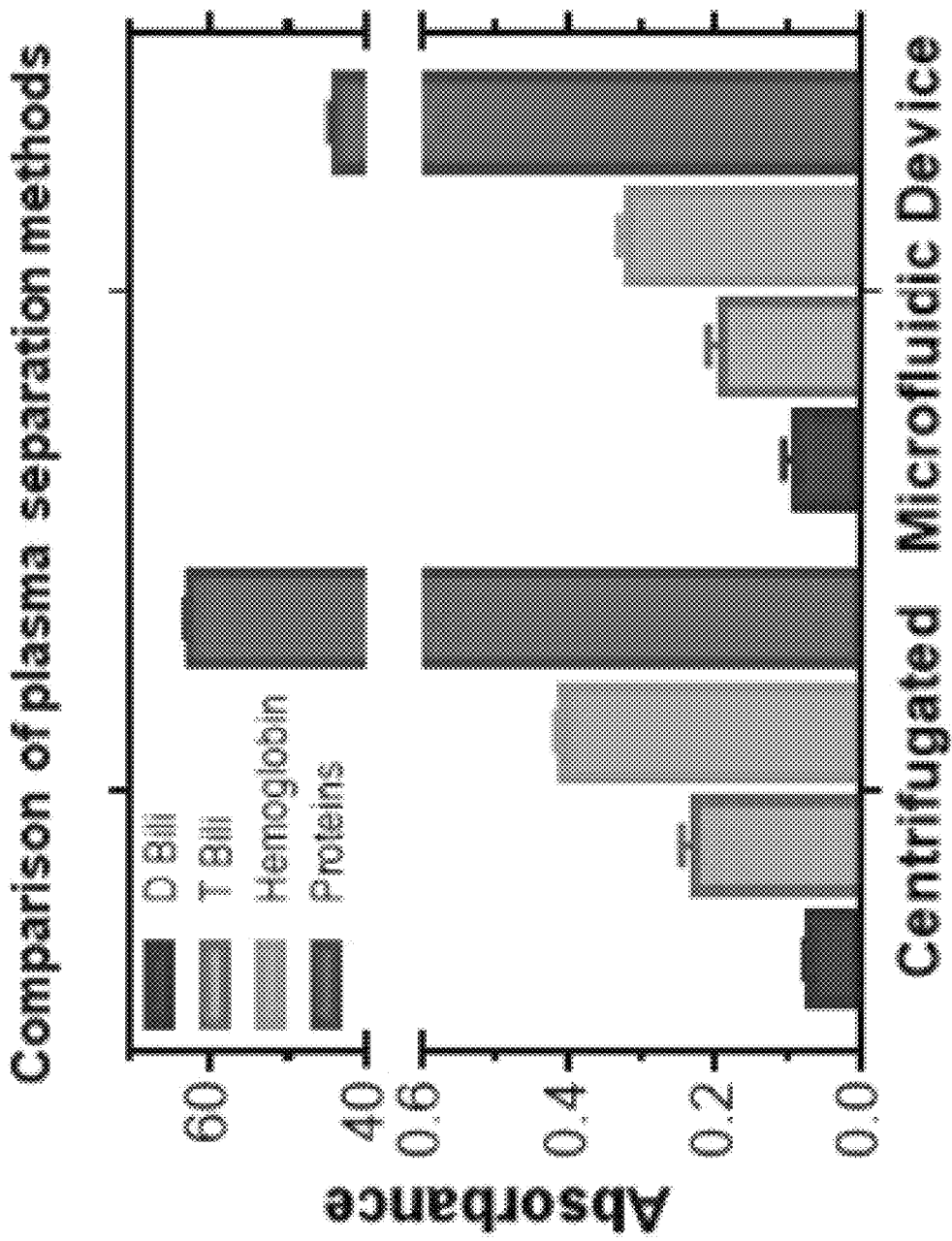
FIG. 3 is a bar graph comparing plasma separation achieved using a plasma separation system provided herein to plasma separation using a centrifugation method.

Prior to plasma biomarkers analysis, plasma separation efficiency was tested. A microfluidic device 100 comprising only the plasma separation module (FIG. 2) was used to evaluate quality of separated plasma compared to a centrifugation method, which is currently a gold standard. Using a spectrophotometer (NanoDrop, Thermo Fisher) and commercially available kits, absorbance for hemoglobin, direct and total bilirubin, and protein abundancy (absorbance at 280 nm) was measured (FIG. 3).

After plasma testing, food dyes were used to show mixing efficiency of active mixing enabled by sequential activation of two microfluidic valves to show homogeneity in all reaction chambers (FIG. 4).

The capability of device to perform enzymatic assays was assessed by using glucose (colorimetric) and lactic acid dehydrogenase (LDH, fluorescent) reactions (FIGS. 5A and 5B).

A glucose assay was tested on plasma separated from 5 μL of whole blood using microfluidic device 10. A glucose solution (8 mM) and PBS 1X were used as positive and negative controls, respectively (FIG. 6).

Results

Plasma separation from whole blood using a microfluidic device exhibited similar results as those obtained when plasma was separated by centrifugation. These results demonstrate that no, or little, cell lysis occurs when using PSM and vacuum. There was a decrease of about 15% in protein abundance for the microfluidic device possibly due to PDM adsorption.

Food dyes allowed for a qualitative analysis of device homogeneity in all reaction chambers, ensuring a complete mixing between both chambers in about 10 minutes. In comparison, diffusion mixing takes up to 3 hours.

For glucose colorimetric assay, a solution containing glucose oxidase, horseradish peroxidase, 4-AAP, and ADOS was injected into the plasma channel and four concentrations of glucose were injected into the reagents chambers (0, 1, 5, and 10 mM). Reaction was carried out by active mixing taking images every minute for a total of 25 minutes. Magenta intensity was analyzed in last images and graphed (FIG. 5A). Analysis showed a very good correlation between glucose concentration and color intensity. LDH assay was carried out in the same fashion, showing capability of the device to perform fluorescence-based assays (FIG. 5B).

Whole blood from a blood bank was separated in the device and tested with a similar methodology as that of the glucose assay, using high concentration tested serum (19 mM) as a positive control. Results showed a good plasma separation with no signs of blood cells in the microchannels. The glucose assay showed an expected lower concentration for the sample glucose compared to the glucose solution (8 mM) positive control, and no signal for the negative control (FIG. 6).

These results confirm the development of a microfluidic device for plasma separation and analysis using small whole blood sample volumes (e.g., from 1 μL to 10 μL of whole blood). Multiple reactions (e.g., two, three, four, five, six, or more) reactions, colorimetric and/or fluorescent, can be carried out in the device simultaneously.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A multiplexed analyte detection system comprising:
   (a) a sample inlet area for receiving a sample,
   (b) a channel fluidly connected to said inlet area via an inlet port and comprising:
      (i) a sample cutoff valve located between said inlet port and a positive pressure channel followed by,
      (ii) a serpentine path followed by,
      (iii) two or more serial sample chambers, wherein each of said two or more serial sample chambers comprises an inflow valve and an outflow valve along said channel, wherein said inflow valves and said outflow valves of each of said two or more serial sample chambers are controlled via a first master valve actuator port, and
      (iv) a vacuum port configured to allow application of a negative pressure to said channel,
   (c) a filter located between said inlet area and said channel and configured to filter said sample to allow a component of said sample to enter said channel when said negative pressure is applied via said vacuum port,
   (d) said positive pressure channel connected to said channel at a location located between said inlet port and said serpentine path, wherein said positive pressure channel comprises:
      (i) a positive pressure control valve located before said channel, and
      (ii) a positive pressure port configured to allow application of a positive pressure to said positive pressure channel, wherein said positive pressure channel is fluidly connected to said channel when said positive pressure control valve is open and is not in fluid communication with said channel when said positive pressure control valve is closed, and (e) two or more reagent chambers, wherein each of said two or more reagent chambers comprises a reaction control valve and is fluidly connected to one of said two or more serial sample chambers when said reaction control valve is open, thereby forming a reaction chamber, and is not in fluid communication with said one of said two or more serial sample chambers when said reaction control valve is closed, wherein said reaction control valves of each of said two or more reagent chambers are controlled via a second master valve actuator port.

2. The system of claim 1, wherein said sample is whole blood.

3. The system of claim 1, wherein said vacuum port is located at the end of said channel.

4. The system of claim 1, wherein said filter is a plasma separation membrane.

5. The system of claim 1, wherein said system comprises reagents for detecting a first analyte if present within a sample chamber, wherein said reagents are located within one of said reagent chambers.

6. The system of claim 5, wherein said first analyte is selected from the group consisting of glucose, bilirubin, an enzyme, a protein, a chemical molecule, and a carbohydrate.

7. The system of claim 5, wherein said system comprises reagents for detecting a second analyte if present within a sample chamber, wherein said reagents are located within a second one of said reagent chambers.

8. The system of claim 7, wherein said second analyte is different from said first analyte, and wherein said second analyte is selected from the group consisting of glucose, bilirubin, an enzyme, a protein, a chemical molecule, and a carbohydrate.

* * * * *

UNITED STATES PATENT AND TRADEMARK OFFICE
CERTIFICATE OF CORRECTION

| | | |
|---|---|---|
| PATENT NO. | : 12,097,494 B2 | Page 1 of 1 |
| APPLICATION NO. | : 17/478154 | |
| DATED | : September 24, 2024 | |
| INVENTOR(S) | : Alan M. Gonzalez Suarez and Alexander Revzin | |

It is certified that error appears in the above-identified patent and that said Letters Patent is hereby corrected as shown below:

In the Specification

Column 1, Line 13, insert:
-- STATEMENT OF FEDERALLY SPONSORED RESEARCH
This invention was made with government support under grant number HD100251 awarded by the National Institutes of Health. The government has certain rights in the invention. --

Signed and Sealed this
First Day of April, 2025

Coke Morgan Stewart
*Acting Director of the United States Patent and Trademark Office*